United States Patent [19]

Caplan et al.

[11] Patent Number: 4,608,199

[45] Date of Patent: Aug. 26, 1986

[54] BONE PROTEIN PURIFICATION PROCESS

[76] Inventors: Arnold Caplan, 1300 Oakridge Dr., Cleveland Heights, Ohio 44121; Glenn T. Syftestad, 3660 Warrensville Center Rd. - #101, Shaker Heights, Ohio 44122

[21] Appl. No.: 591,505

[22] Filed: Mar. 20, 1984

[51] Int. Cl.⁴ .................... C07K 15/06; C07K 15/20; C07K 3/20; C07K 3/28
[52] U.S. Cl. .................................. 530/414; 530/416; 530/417; 424/95; 514/21
[58] Field of Search ....................... 260/123.7, 112 R; 424/95; 514/21

[56] References Cited

U.S. PATENT DOCUMENTS

| | | | |
|---|---|---|---|
| 4,294,753 | 10/1981 | Urist | 260/112 R |
| 4,434,094 | 2/1984 | Seyedin et al. | 260/112 R |
| 4,455,256 | 6/1984 | Urist | 260/112 R |

OTHER PUBLICATIONS

Proc. Natl. Acad. Sci., USA, 76, No. 4, 1828–1832 (1979), Urist et al.
Cell., vol. 26, 99–105 (1981), Termine et al.
Clin. Orthopedics, No. 153 (1980), pp. 232–240, Hanamura et al.
Proc. Soc. Exptl. Biol. & Med. 162, 48–53 (1979), Urist et al.
Proc. Soc. Exptl. Biol. & Med. 173, 194–199 (1983), Urist et al.
J. of Biol. Chem., Oct. 25, 1981, pp. 10403–10408, Termine et al.
Chemistry & Biology of Mineralized Connective Tissues, 1981, pp. 597–606, Conover et al.
Clin. Orthopedics, No. 162 (1982), Urist et al.
Proc. Natl. Acad. Sci., USA, 81, 371–375 (Jan. 1984), Urist et al.
Exp. Cell. Res. 62: 341–355 (1970), Caplan.
Urist, Bone: Formation by Autoinduction, *Science* 150: 893–899, 1965.
Iwata, et al., Protein Polysaccharides of Bone Morphogenetic Matrix, *Clin. Ortho. Related Res.* 84: 257–274, 1974.
Urist, et al., Bone Morphogenesis in Implants of Insoluble Bone Gelatin, *Proc. Nat'l Acad. Sci. U.S.A.* 70: 3511–3515, 1973.
Urist, et al., Preservation and Biodegration of the Morphogenetic Property of Bone Matrix, *J. Theor. Biol.* 38: 155–168, 1973.
Hanamura, et al., Solubilized Bone Morphogenetic Protein (BMP) from Mouse Osteosarcoma and Rat Demineralized Bone Matrix, *Clin. Ortho. Related Res.* 148: 281–292, 1980.
Seyedin, et al., In Vitro Induction of Cartilage-Specific Macromolecules by a Bone Matrix, *J. Cell. Biol.* 97: 950–953, 1983.
Urist, "The Origin of Cartilage; Investigations in Quest of Chondrogenic DNA", in *Cartilage: Development, Differentiation and Growth*, (B. K. Hall, ed.) vol. 2, pp. 2–86, Academic Press, N.Y., 1983.
Anastassiades, et al., Effect of Solubilized Bone Matrix Components on Cultured Fibroblast Derived From Neonatal Rat Tissues, *Calcif. Tiss. Res.* 26: 173–179, 1978.
Termine, et al., Osteonectin: Bone Proteoglycan, and Phosphophoryn Defects in a Form of Bovine Osteogenesis Imperfecta, *Proc. Nat'l Acad. Sci. U.S.A.* 81: 2213–2217, 1984.
Urist, et al., Transmembrane Bone Morphogenesis Across Multiple-Walled Diffusion Chambers, *Arch. Surg.* 112: 612–619 (1977).
Sampath, et al., Extracellular Bone Matrix-Derived Growth Factor, *Exp. Cell. Res.* 142: 460–464 (1982).
Minkin, et al., Mononuclear Phagocytes and Bone Resorption: Identification and Preliminary Characterization of a Bone-Derived Macrophage Chemotactic Factor, *Metabolic Bone Disease and Related Res.* 2: 363–369, 1981.
Malone, et al., Recruitment of Osteoclast Precursors by Purified Bone Matrix Constituents, *T. Cell Bio.* 92: 227–230, 1982.
Puzas, et al., Endogenous Inhibitor of Bone Cell Proliferation, *Proc. Soc. Exp. Bio. and Med.* 166: 113–122, 1981.
Farley, et al., Purification of a Skeletal Growth Factor From Human Bone, *Biochem.* 21: 3502–3507, 1982.
Nogami, et al., Diffusion of Bone Morphogenetic Activity From the Residue of Collagenase Digested Bone Matrix Gelatin Through Interstitial Fluid, *Clin. Ortho. and Related Res.* 115: 268–273, 1976.
Canalis, et al., Stimulation of DNA and Collagen Synthesis by Autologons Growth Factor in Cultured Fetal Rat Calvaria., *Science* 210: 1021–1023, 1980.

*Primary Examiner*—Howard E. Schain
*Attorney, Agent, or Firm*—Watts, Hoffmann, Fisher & Heinke Co.

[57] ABSTRACT

A process of extracting and purifying a bone protein capable of stimulating chondrogenic expression in undifferentiated cells in culture. The purification process is monitored at various stages by bioassaying the bone protein for chondrogenic activity in embryonic limb bud mesenchymal cell cultures.

5 Claims, No Drawings

BONE PROTEIN PURIFICATION PROCESS

TECHNICAL FIELD

This invention relates generally to a bone protein purification process, and more specifically to a process for extracting and purifying soluble bone protein capable of stimulating chondrogenesis.

BACKGROUND ART

Bone matrix is known to contain a number of proteins which influence the behavior of various cell types. Some bone matrix proteins stimulate or inhibit the replication of bone cells (Farley et al Biochem., 21: 3508-3513, 1982; Sampath et al, Experimental Cell Res. 142: 460-464, 1982, and Puzas et al, Proc. Soc. Exp. Bio. and Med. 166: 113-122, 1981). Other bone matrix proteins stimulate collagen synthesis in bone cells (Canalis et al, Science 210: 1021-1023, 1980). Bone matrix, proteins such as Alpha$_2$HS glycoprotein, osteonectin, and Type 1 collagen are chemotatic factors for monocytes and macrophages (Malone et al, J. Cell Bio. 92: 227-230, 1982; Minkin et al, Metabolic bone Disease and Related Res. 2: 363-369, 1981).

Cartilage, but not bone, will form in pieces of muscle grown directly upon demineralized bone matrix. Demineralized bone matrix or bone matrix gelatin implanted in muscle pouches in vivo or implanted in diffusion chambers in muscle pouches in vivo is capable of recruiting native mesenchymal cells and inducing bone formation (Urist et al, Arch. Surg. 112: 612-621, 1977; Nogami et al, Clin, Orthopaedics 103: 235-247, 1977).

U.S. Pat. No. 4,294,753 discloses a process for obtaining a water-insoluble bone morphogenic protein (BMP) whose action is analogous to bone matrix gelatin in that it stimulates cartilage and bone formation when implanted in a muscle pouch in vivo.

DISCLOSURE OF THE INVENTION

This invention provides a novel process for obtaining a soluble purified bone protein that causes undifferentiated cells to differentiate in culture. The product of the invention has potential human use in enhancing the rate of bone ingrowth into limb protheses, thereby eliminating the use of artificial cements. It also has potential human use in stimulating or enhancing the regeneration of damaged or diseased skeletal tissue, including periodontal defects.

This application is related to copending applications Ser. No. 591,440 filed 3-20-84 and Ser. No. 628,168 filed 7-5-84 which disclose processes or techniques for delivering the soluble bone protein to anatomical sites. The disclosures of both of said copending applications are incorporated herein by reference.

In the process of the invention each step of the purification process is combined with a bioassay that identifies the way in which the bone protein influences cells by its ability to stimulate cartilage formation in cultured cells, such as embryonic mesenchymal cells. Chick embryo limb bud mesenchyme cells, for example, are capable of differentiating in culture into either cartilage or bone or connective tissue fibroblasts. The emergence of one of these cell types is dependent upon plating density and nutrient medium composition. Since cultured mesenchymal cells will form a predictable number of chondrocytes when grown under specific conditions, this in vitro system can be utilized as a bioassay for substances which enhance or inhibit the limb mesenchyme-to-chondrocyte transition (Caplan, Exp. Cell Res. 62: 341-355, 1970). A limb mesenchymal cell system is, therefore, ideal for identifying the desired protein found in bone in that the purification process can be focused on those fractions with the desired modulating activity.

In a preferred embodiment, the invention provides a process of purifying a mixture of bone matrix protein to obtain a protein capable of enhancing chondrogenesis which includes the steps of fractionating the mixture of bone matrix protein a plurality of times, bioassaying all fractions in undifferentiated cells at the conclusion of each fractionating step in order to identify the fractions having the greatest cell differentiating activity, and using only those identified fractions having the greatest cell differentiating activity in the next succeeding fractionating step.

In an especially preferred embodiment, the invention provides a process of purifying a mixture of bone matrix protein to obtain a 30 to 32K dalton protein which includes the steps of preparing a guanidinium chloride extract of demineralized, defatted bone, dialyzing the extracted mixture of bone matrix protein until it is substantially salt-free, separating the water soluble retentate from the water insoluble precipitate, absorbing the water soluble retentate with an anionic exchanger and desorbing by eluting with a substantially linear salt gradient, bioassaying fractions eluted by the salt gradient in cultured undifferentiated cells to identify fractions having the greatest chondrogenic activity, passing only those identified fractions having the greatest chondrogenic activity over a molecular sieve, bioassaying fractions passed over the molecular sieve in cultured undifferentiated cells to identify fractions having the greatest chondrogenic activity, repeating the steps of passing over a molecular sieve and bioassaying to identify fractions, passing only those identified fractions having the greatest chondrogenic activity over lectin coupled gel, collecting the eluate from the lectin coupled gel in one fraction and passing the fraction over a molecular sieve to isolate a single 30 to 32K dalton protein.

Other features and a fuller understanding of the invention will be had from the following detailed description of a best mode.

BEST MODE FOR CARRYING OUT THE INVENTION

The following example illustrates the invention and describes the process of extracting and purifying from bone a soluble protein capable of stimulating chondrogenesis.

Diaphyseal cortical bone shaft from beef femurs were cut into 2-3 mm thickness rings and demineralized for 7 days in 0.6M hydrochloric acid at 4° C. The acid was decanted and the bone matrix washed in distilled water overnight at 4° C. The matrix was defatted by a 2 hour extraction in chloroform-methanol (1:1). The solvent was decanted and the matrix air dried overnight. The matrix was extracted in 4M guanidinium chloride for three days at 4° C. In alternate procedures or examples of the invention, the matrix has been extracted with 1M NaCl for five days at 37° C. The resultant solvent-protein mixture was dialyzed at 4° C. in 12,000 to 14,000 molecular weight pore size tubing against step wise decreasing ionic strength buffers, first against 0.5M NaCl in 50 mM Tris, pH 7, then 0.15M NaCl in 50 mM Tris, pH 7; and finally against distilled water until the dialysate was chloride free. A cold water-insoluble precipitate which formed during dialysis was discarded. The cold water soluble components in the retentate were lyophilized.

The lyophilized water soluble retentate was further purified by resuspension in 50 mM Tris buffer, pH 8.0 and absorbed on a DEAE-Sephacyl anionic exchange column (35×1.5 cm). The column was first eluted with Tris buffer (70 ml) to collect unbound protein and then with a linear salt gradient of 0.1 to 1.0M NaCl (1.1 ml/min; total gradient volume=250 ml). Tubes containing 1.0 ml of eluent were collected and pooled into 6 fractions and dialyzed against cold distilled water. Fraction VI, desorbed between 0.6 to 1.0 molar NaCl (Tube numbers 270-320) contain the chondrogenic activity. This protein fraction is hereinafter called Protein $A_{VI}$.

Protein $A_{VI}$ was resuspended in 4M guanidinium chloride and was passed through a Sepharose CL-6B molecular sieve column (100×0.5 cm) equilibrated with 4M guanidinium chloride. 0.6 ml fractions were collected (total volume=50 ml). The effluent protein concentration was monitored on a Gilson recording spectrophotometer at 280 nm. Three broad protein peaks were observed and the individual collection tubes corresponding to each peak were pooled, dialyzed against cold water and lyophilized. Fractions corresponding to the second peak were active (Tube numbers 31-53). This protein fraction is hereinafter called Protein $B_{II}$.

Protein $B_{II}$ was then rechromatographed through the same column. The fraction containing the greatest biological activity (Tube numbers 42-53) were dialyzed and lyophilized. This protein is hereinafter called Protein $C_{III}$.

The lyophilized Protein $C_{III}$ was resuspended in 1.0M NaCl in Tris buffer, pH 7.0 and passed through a Sepharose-Conconavalin A column (10 cm×0.5) equilibrated with 1.0 NaCl. (Total Volume=15 ml). The conconavalin—A bound only contaminating glycoproteins. The active factor passed through the column and the eluate was collected in one fraction, dialyzed, and lyophilized. This protein is hereinafter called Protein $D_I$.

Protein $D_I$, which contained 3 prominent protein components as assessed by polyacrylamide gel electrophoresis, was re-cycled through a Sepharose CL-6B column to isolate a single 30-32k dalton component with in vitro chondrogenic stimulating activity. This protein, which is referred to as Protein $E_1$, has been found effective in stimulating chondrogenesis in undifferentiated cells.

The bioassay for chondrogenic activity in each of the purification steps above utilized a cell culture system previously reported by Caplan, *Exp. Cell Res.* 62: 341-348 (1970).

The lyophilized water-soluble proteins from each purification step were resuspended in warm water (37° C. to 45° C.) and added to serum supplemented nutrient medium (Eagle's Minimum Essential Medium plus 5% chick embryo extract plus 3% fetal calf serum plus 7% horse serum) at decreasingly smaller doses depending upon the degree of purity. For the least pure protein, Protein $A_{VI}$, maximal chondrogenic activity was detected at Lowry protein concentrations ranging from 40-60 ug/ml; and for Protein $E_1$ at 1 to 5 ug/ml.

A similar increase in limb bud cell chondrogenesis was observed when cultures were maintained in serum-free medium composed of the following defined substances: a basal medium containing Ham's F-12 and Dulbecco's modified Eagles to which is added insulin (5 ug/ml), transferrin (5 ug/ml), hydrocortisone (100 mM) and 0.1% bovine serum albumen. The quantity of soluble bone protein necessary to produce a significant stimulation in cartilage formation was approximately 0.125 to 0.100 times that required in similar cultures grown in serum supplemented medium.

1 ml of nutrient solution containing 2.0 to $2.5 \times 10^6$ enzymatically isolated embryonic (HH stage 23-24) chick limb bud mesenchymal cells was plated onto 35 mm tissue culture dishes. 5 ug of Protein $E_1$ was added to the culture dishes 18 to 24 hours after plating the cells. The cells were incubated at 37° C. in 5% $CO_2$ for 7-8 days. The chondrogenic effect was documented by visual observation of living cultures using a phase contact inverted microscope, by Toludine Blue staining of fixed day 8 cultures and by radioactive precursor uptake into cartilage-specific proteoglycans.

A 7 day exposure to Protein $E_1$ stimulated undifferentiated limb bud mesenchyme to form cartilage in a dose dependent manner.

In 35 mm plates, the reaction had the following characteristics:

1. An initial seeding density of approximately $2 \times 10^6$ cells was necessary to observe the chondrogenic response.

2. A maximal chondrogenic response was observed when cultured mesenchyme were exposed to Protein $E_1$ during the interval between 0.5-2.5 days following plating. The stimulation of chondrogenesis was slight if exposure to the protein was later than 2.5 days after plating.

3. A maximal chondrogenic response was observed when cultured mesenchyme were exposed to Protein $E_1$ for seven continuous days. Exposure times of 1-2 days resulted in only a slight increase in chondrogenesis (i.e., 1.5-2 times the $^{35}S-SO_4$ incorporation).

4. The appearance of morphologically recognizable chondrocytes occured on days 5-6 and chondrocytes continued to develop so that over 90% of the culture dish was covered with cartilage by day 8. This represented a maximum response and correlated with a 4-5 fold increase in cell-layer associated $^{35}S-SO_4$ uptake/ug DNA and an intensely metachromatic Toludine Blue staining pattern when compared to untreated cells.

Modifications of the above invention and materials and procedures employed therein which are obvious to persons of skill in the art are intended to be within the scope of the following claims.

We claim:

1. A process of purifying bone matrix proteins to obtain a cold-water-soluble 30 to 32k dalton protein capable of stimulating cartilage formation in mesenchymal-like cells comprising the steps of:
    (a) preparing a guanadinium chloride extract of demineralized, defatted bone;
    (b) dialyzing the guanidinium chloride soluble extract against decreasing ionic strength buffers down to water until it is substantially salt-free;
    (c) separating the cold-water-soluble proteins from the cold-water-insoluble proteins present in the retentate;
    (d) adsorbing the cold-water-soluble proteins in the retentate with an anionic exchanger at about pH 8.0 and desorbing by eluting with a substantially linear salt gradient;
    (e) assaying fractions eluted by the salt gradient in undifferentiated mesenchymal-like cell cultures to identify fractions having the greatest chondrogenic activity;
(f) passing only those identified fractions having the greatest chondrogenic activity over a molecular sieve column;
(g) assaying fractions passed over the molecular sieve in undifferentiated mesenchymal-like cells to identify fractions having the greatest chondrogenic activity;
(h) repeating steps (f) and (g);
(i) passing only those identified protein fractions having the greatest chondrogenic activity over concanavalin—A coupled gel;
(j) collecting the unbound protein from step (i) in one fraction; and
(k) passing the unbound protein from step (j) over a molecular sieve column to isolate a single 30 to 32k dalton protein.

2. The purified protein produced by the process of claim 1.

3. A process of purifying bone matrix proteins to obtain a cold-water-soluble 30 to 32k dalton protein capable of stimulating cartilage formation in embryonic cells comprising the steps of:
(a) preparing a guanadinium chloride extract of demineralized, defatted bone;
(b) dialyzing the guanidinium chloride soluble extract against decreasing ionic strength buffers down to water until is is substantially salt-free;
(c) separating the cold-water-soluble proteins from the cold-water-insoluble proteins present in the retentate;
(d) absorbing the cold-water-soluble proteins in the retentate with an anionic exchanger at about pH 8 and desorbing by eluting with a substantially linear salt gradient;
(e) assaying fractions eluted by the salt gradient in undifferentiated embryonic limb bud mesenchymal cell culture to identify fractions having the greatest chondrogenic activity;
(f) passing only those identified fractions having the greatest chondrogenic activity over a molecular sieve column;
(g) assaying fractions passed over the molecular sieve in undifferentiated embryonic limb bud cells to identify fractions having the greatest chondrogenic activity;
(h) repeating steps (f) and (g);
(i) passing only those identified protein fractions having the greatest chondrogenic activity over concanavalin—A coupled gel;
(j) collecting the unbound protein from step (i) in one fraction; and
(k) passing the unbound protein from step (j) over a molecular sieve column to isolate a single 30 to 32k dalton protein.

4. The highly purified protein extracted from bone matrix by the process of claim 1 having the following characteristics:
(a) molecular weight of 30–32k daltons as assessed by electrophoresis;
(b) solubility in substantially pure water at a temperature of 4° C.;
(c) affinity for anionic exchangers at about pH 8.0;
(d) non-affinity for concanavalin—A; and
(e) activity as a stimulator of chondrogenesis in undifferentiated cells.

5. The highly purified protein extracted from bone matrix by the process of claim 3 having the following characteristics:
(a) molecular weight 30–32k daltons as assessed by electrophoresis;
(b) solubility in substantially pure water at a temperature of 4° C.;
(c) affinity for anionic exchangers at about pH 8.0;
(d) non-affinity for concanavalin—A; and
(e) activity as a stimulator of chondrogenesis in undifferentiated cells.

* * * * *